United States Patent [19]

Kawai

[11] Patent Number: 5,080,586

[45] Date of Patent: Jan. 14, 1992

[54] APICAL FORAMEN POSITION DETECTOR FOR USE IN DENTAL TREATMENT

[75] Inventor: Akira Kawai, Tokyo, Japan

[73] Assignee: Osada Research Institute, Ltd., Tokyo, Japan

[21] Appl. No.: 586,940

[22] Filed: Sep. 24, 1990

[51] Int. Cl.$^5$ ............................................. A61B 5/05
[52] U.S. Cl. ...................................... 433/32; 128/776; 128/734
[58] Field of Search ............................ 433/27, 32, 72; 128/776, 777, 734

[56] References Cited

U.S. PATENT DOCUMENTS

| | | | |
|---|---|---|---|
| 3,916,529 | 11/1975 | Mousseau | 433/72 |
| 3,993,044 | 11/1976 | McGuffin | 433/27 |
| 4,273,531 | 6/1981 | Hasegawa | 433/27 |
| 4,447,206 | 5/1984 | Ushiyama | 433/32 |

Primary Examiner—Kyle L. Howell
Assistant Examiner—Robert L. Nasser, Jr.
Attorney, Agent, or Firm—Jordan and Hamburg

[57] ABSTRACT

There is disclosed a device for detecting the position of an apical foramen of a tooth's root by measuring a change in the impedance between a measuring needle inserted into a tooth's root canal and an electrode abutting on oral mucosa. This device includes a circuit for generating two kinds of different frequency signals, detection circuits for detecting a change in the impedance in response to the respective frequencies and a "difference" detection circuit for successively comparing outputs of the detection circuits and for producing a "difference" signal, and a feed back circuit for feeding an output of the "difference" detection circuit to one of the input terminals of the "difference" detection circuit so as to equalize its two inputs by addition or by subtraction and thereby to make its output equal to zero. Furthermore, the device is provided with a means for announcing that the output of the "difference" detection circuit is set to zero, and an indicating means for informing that the output of the "difference" detection circuit has reached the specified value when the measuring needle is inserted further into the tooth's root canal after the above-mentioned zero setting. The position of the apical foramen is considered to be the location of the measuring needle's tip when the output of the "different" detection circuit reaches the specified value.

8 Claims, 6 Drawing Sheets

APICAL FORAMEN POSITION DETECTOR FOR USE IN DENTAL TREATMENT

BACKGROUND OF THE INVENTION

The present invention relates to a device for detecting the position of an apical foramen of a tooth root for use in dental treatment and more particularly to a method for achieving zero-adjustment of the apical foramen position detector.

In dental treatment, it is usual to treat any vital tooth without extracting it by enlarging, cleaning and disinfecting its root canal and then by filling the root canal with a filling. For a root canal treatment it is necessary to detect accurately the position of the end of the root canal (hereinafter referred to as "an apical foramen").

A device for electrically detecting the apical foramen's position is disclosed in the Japanese laid open patent publication No. 174144/85. The device is such that two AC voltages having different frequencies, for example of 1KHz and 5KHz, are applied to an electrode abutting on oral mucosa and a measuring needle inserted into the root canal of a tooth. The two AC voltages of different frequencies are generated by a pulse generator with a standard frequency preset to 1KHz, and its output is supplied to a measuring needle and an electrode respectively. A resistor is connected between the electrode and the pulse generator and both terminals of the resistor are connected to respective amplifiers. One of the amplifiers is connected at its output to a filter for selecting 1KHz, the output of which is rectified through a rectifier circuit and connected to one of the input terminals of a comparator. The output of the other amplifier is connected to a filter for selecting 5KHz, the output of which is connected through a rectifier circuit to the other input terminal of the comparator. The comparator's output is connected to an amplifier, the output of which is then connected to a display unit. When a dentist slowly inserts the measuring needle into the root canal of a patient's tooth, an impulse signal of 1KHz and an impulse signal of 5KHz, generated by the pulse generator, are multiplexed within a specified period and released. In response to the output signal and the impedance between the measuring needle and the electrode, a weak current is generated which flows through the resistor and is amplified by the amplifiers respectively.

While only a weak current responding to the impulse signal of 1KHz passes through one filter, only a weak current responding to the impulse signal of 5KHz passes through the other filter. While the measuring needle is being moved in the tooth's root canal, the impedance between the measuring needle and the electrode is kept substantially constant, thereby each voltage responding to an input signal's frequency, i.e. an output signal through one of the filters is kept substantially constant. When the measuring needle is inserted further and is nearly out of the root canal's end, the impedance between the measuring needle and the electrode decreases to correspondingly increase the two output voltages of the corresponding filters in such a way that one output voltage changes slowly and the other changes quickly depending upon their frequency responses.

Attention is paid to the difference between both output voltages. Although the output voltages vary at different rates due to their different responses to the input frequencies, their changing ratios increase to the maximum when the measuring needle has reached the apical foramen. Accordingly, the position of the apical foramen can be detected as the point whereat the minimum difference of the output voltages is obtained.

However, to correctly determine the above-mentioned minimum point it is irrevocably necessary to advance the needle tip beyond the apical foramen's position. The advancement of the measuring needle past the root's apex is undesirable and may cause the overpenetration of the needle through the tooth's root canal.

SUMMARY OF THE INVENTION

It is an object of the present invention to provide a device for electrically detecting the position of a root canal's apical foramen in order to prevent a measuring needle from penetrating beyond the apical foramen's apex.

It is another object of the present invention to provide a device for detecting the position of a root canal's apical foramen and capable of detecting the apical foramen's position in such a way that two voltages having different frequencies, are applied between a measuring needle inserted into a tooth's root canal and an electrode piece abutting to the oral mucosa, the apical foramen's position being detected as a point whereat the difference between the two output voltages due to their frequency components, becomes constant in value.

It is another object of the present invention to provide a zero-adjusting device whereby the difference between two output voltages, due to their respective frequency components, is adjusted to zero prior to the detection of the apical foramen's position.

DESCRIPTION OF THE PREFERRED EMBODIMENTS

Figure 1:
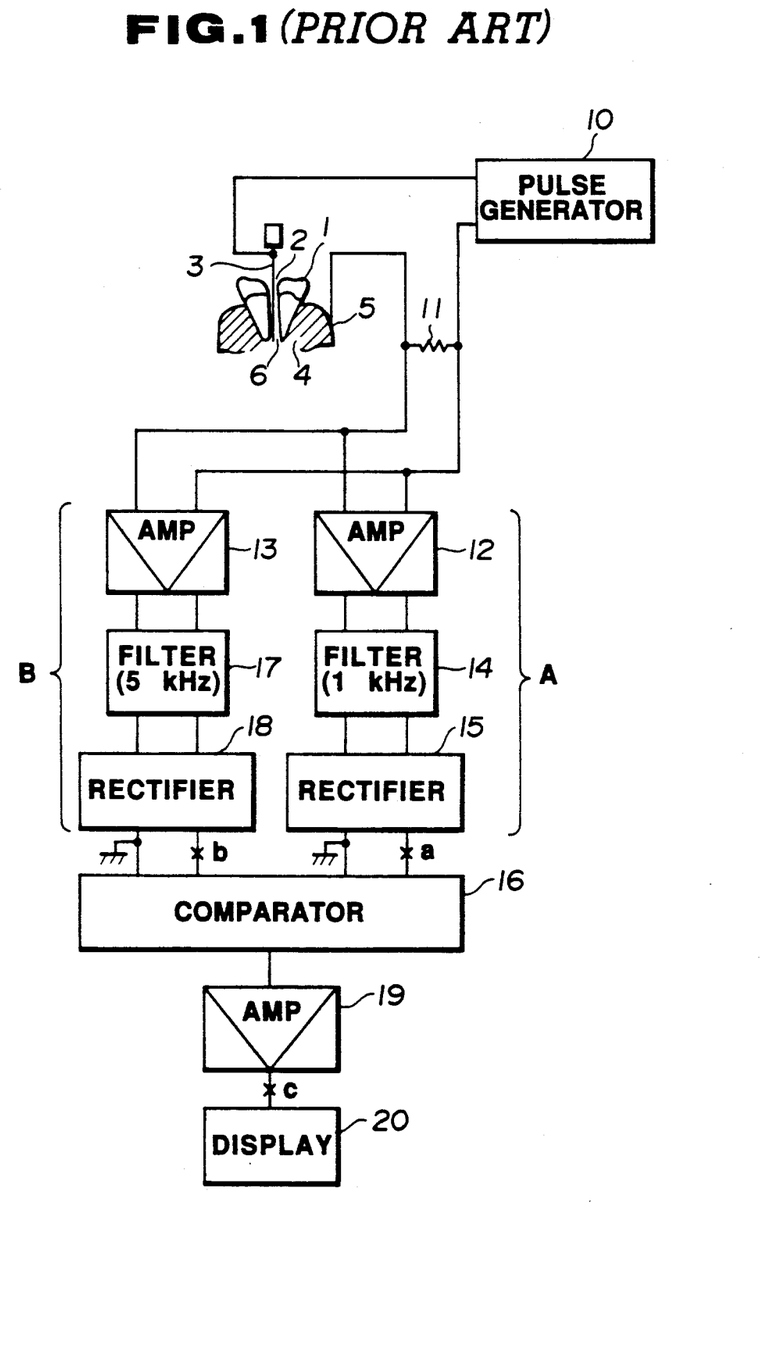
FIG. 1 is a view for explaining an example of a conventional detector for detecting the position of the apical foramen of a tooth.

FIG. 1 is a view showing an example of the prior art for electrically detecting the position of a tooth's apical foramen, disclosed in the Japanese laid open patent publication No. 174144/85. As shown in FIG. 1, the prior art seeks to insert a reamer, serving as a measuring needle 3, into a root canal 2 of a tooth 1 and to attach an electrode 5 onto oral mucosa and then to apply therebetween two AC voltages of current having respectively different frequencies, as for example of 1KHz and 5KHz for detecting the position of the apical foramen 6. In FIG. 1, numeral 10 designates a pulse generator for generating two different frequencies, which is connected to the measuring needle 3 and the electrode piece 5. A resistor 11 is inserted between the electrode 5 and the pulse generator 10 and both ends are connected to amplifiers 12 and 13 respectively. The output of the amplifier 12 is connected to a filter 14 for selecting 1KHz and then to a rectifier 15 for rectifying the filtered output and the rectified output is further connected to one of the input terminals of a comparator 16. The output of the amplifier 13 is connected to a filter 17 for selecting 5KHz and then to a rectifier 18 for rectifying the filtered output and the rectified output is further connected to the other input terminal of a comparator 16. That is to say, there are two circuits A and B formed: circuit A composed of the amplifier 12, the filter 14 and the rectifier 15 serves as a detection circuit which responds to the frequency of 1KHz, and circuit B composed of the amplifier 13, the filter 17 and the rectifier 18 serves as a detection circuit which responds to the frequency of 5KHz. The output of the comparator 16 is connected to an amplifier 19 which may be connected at its output to a display unit 20.

Figure 2:
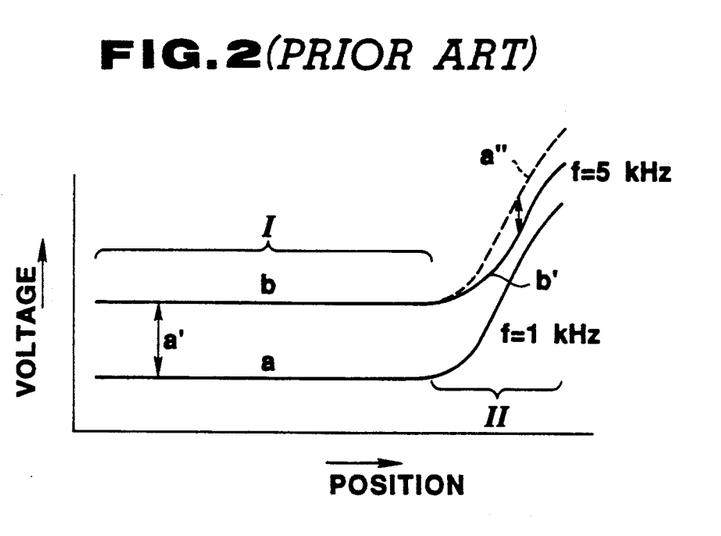
FIG. 2 shows waveforms of volts measured respectively at points "a" and "b" shown in FIG. 1.

FIG. 2 is a diagram showing the output voltage of the rectifier 15, i.e. a voltage at point "a", and an output voltage of the rectifier 18, i.e. a voltage at point "b" shown in FIG. 1, in relation to the positions of the measuring needle 3 inside the root canal 2 plotted along the X-axis. In the circuit block diagram of FIG. 1, it is supposed that the basic frequency of the pulse generator 1 is set to 1KHz. At this point, a dentist slowly inserts the measuring needle 3 into the patient's root canal. At the same time, the pulse generator 10 produces an impulse signal of 1KHz and an impulse signal of 5KHz which are multiplexed with each other at a specified time period and are output. A weak current generated in response to these output signals and an impedance between the measuring needle 3 and the electrode 5 flows through the resistor 11 and is amplified by the amplifiers 12 and 13 respectively.

Only a weak current responding to the impulse signal of 1KHz passes through the filter 14, and the output at point "a" shown in FIG. 1 becomes as shown by (a) in FIG. 2. Only a weak current responding to the impulse signal of 5KHz passes through the filter 17, and the output at point "b" shown in FIG. 1 becomes as shown by (b) in FIG. 2.

While the measuring needle 3 is being moved within the root canal 2, the impedance between the measuring needle 3 and the electrode piece 5 is kept substantially constant, thereby the outputs of points "a" and "b", responding to the respective frequencies of the input signal, have substantially linear forms as shown in range I of FIG. 2. In this condition, the measuring needle 3 is inserted further into the root canal 2 until its tip nearly comes out of the apical foramen, the impedance between the measuring needle 3 and the electrode piece 5 decreasing. In response to said impedance change, two outputs of points "a" and "b" increase in such a manner that the output (a) changes slowly and the output (b) changes quickly depending upon their respective frequency characteristics as shown in the range II of FIG. 2.

Now, the difference between the outputs (a) and (b) is examined. Although the changing rates of the outputs (a) and (b) are different, due to their different frequency responses to the input, they reach their maximum point when the measuring needle 3 becomes near to the apical foramen 6. Accordingly, the position of the apical foramen 6 can be detected as a point whereat the minimum difference between the outputs (a) and (b) is obtained.

Figure 3:
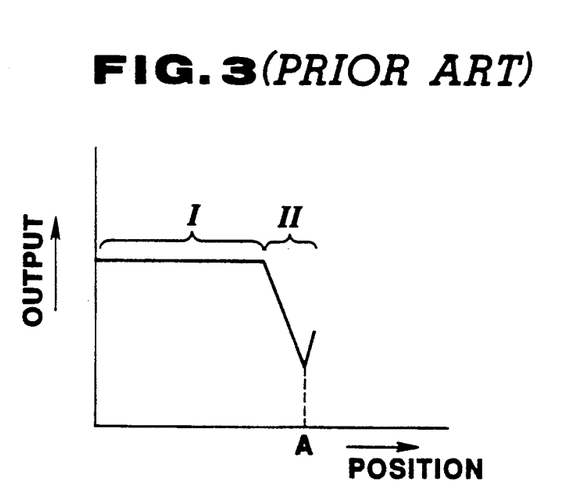
FIG. 3 shows voltage wave-form measured at the point "c" shown in FIG. 1.

The comparator 16 compares the pairs of outputs (a) and (b) to produce a differential which is amplified by amplifier 19 to a specified level and then is output from the output terminal "c" of the amplifier 19 as a waveform shown in FIG. 3. In FIG. 3, in the region I corresponding to the region I shown in FIG. 2, the difference between the outputs (a) and (b) is substantially constant, and in the region II corresponding to the region II shown in FIG. 2, the difference between the outputs (a) and (b) decreases and reaches the minimum value at the position of the apical foramen (at the point "A" in FIG. 3). This output (c) is visually displayed on a cathode-ray tube or a meter of the display unit 20, and furthermore the minimum point "A" corresponding to the position of the apical foramen is audibly announced by a buzzer or the like, thereby the dentist may easily know the position of the apical foramen of the tooth's root during the root canal treatment.

Although the above-mentioned embodiment describes a case of input frequencies of 1KHz and 5KHz being applied, clinical tests also show that the same effect can be obtained in the input frequency range of 1KHz to 1MHz.

As mentioned above, according to the prior art it is impossible to correctly detect the position whereat the differential output reaches a minimum (the point "A" in FIG. 3) without advancing the measuring needle's tip a little beyond the position of the apical foramen.

However, the advancement of the measuring needle beyond a root's apex is undesirable in itself and may cause the over-penetration of the measuring needle through a tooth's root canal.

The present invention was made in order to solve the above-mentioned problem in such a way that the position of the tooth's apical foramen may be detected at a specified value of the differential output.

Figure 4:
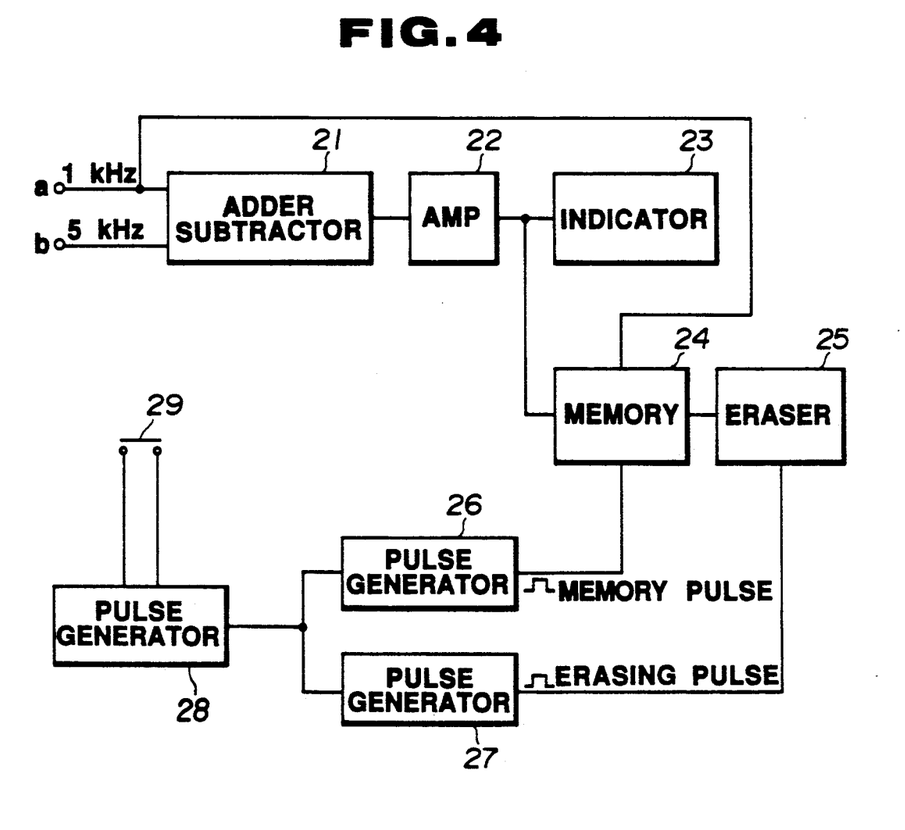
FIG. 4 is a view for explaining the embodiment of an apical foramen's position detector embodied in the present invention.

FIG. 4 is a block diagram for explaining the construction of a device embodying the present invention. The device for detecting the position of an apical foramen by utilizing a change in an impedance between a measuring needle 3 and an electrode piece 5 which are similar to those shown in FIG. 1, and comprises a circuit 10 for generating two kinds of signals having different respective frequencies: detection circuits A and B for detecting a change in the impedance, in response to the respective frequencies, and a circuit 16 for successively producing a different signal by comparing outputs of the detection circuits, and is characterized in that one of the detection circuits A and B is provided with a memory circuit 24 for superimposing a bias signal and a reset signal generating circuit 29 and a value to be stored in the memory circuit 24 is set according to a difference in output of the circuit 16 (21) in response to the reset signal, thereby making it possible to know the position of an apical foramen as a position whereat an output of the circuit 16 (21) for producing a different signal becomes a specified value. Detection of the specified value may be conducted not only by taking the reading of a meter 23 or the like but also audibly or visually by the use of a buzzer or a visual alarm to be connected to the output of a circuit for the detection of a threshold limit value.

Referring to FIG. 2 the output state of the circuit for detection of a difference is explained again. As described above, signals (a) and (b) are output signals, for example, of 1KHz and 5KHz respectively. A voltage (a') which corresponds to a difference between outputs (a) and (b) in the region I is applied as a biased value to the output (a), thereby the outputs (a) and (b) become equal to each other in the region I, and they become apart from each other in region II as shown by curves (a") and (b') respectively as the measuring needle 3 moves forward. The present applicant found that according to the clinical data the difference between the values curves (a") and (b') corresponding to the aforementioned minimum difference between the outputs (a) and (b) is a substantially constant with no variation among individuals (i.e. the current values measured at the apexes of the roots of teeth are almost the same for all patients).

Consequently, according to the present invention, both outputs are made equal to each other in region I by adding (or subtracting) the difference as a bias to (or from) one of the output signals having respective frequencies and the apical foramen is detected by the output signal when the detection circuit reaches a specified constant value.

Figure 5:
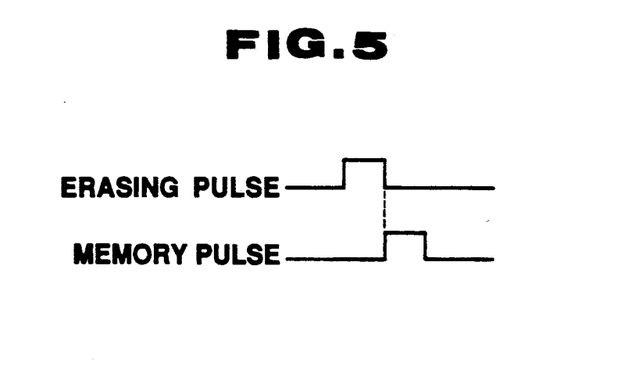
FIG. 5 is a view showing the correlation between an erasing pulse and a storing pulse.
Figure 6A:
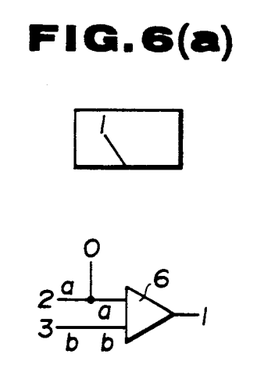
FIGS. 6 and 7 are views for explaining the operations of the embodiment shown in FIG. 4.
Figure 6B:
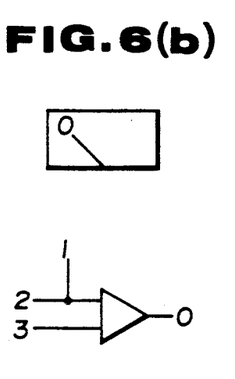
Figure 6C:
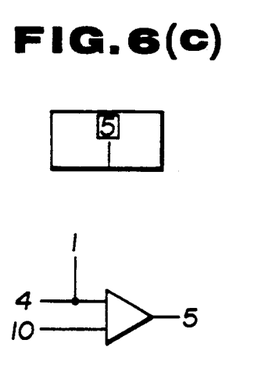
Figure 7A:
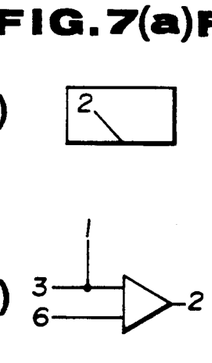
Figure 7B:
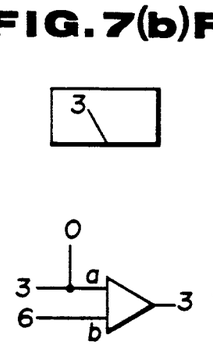
Figure 7C:
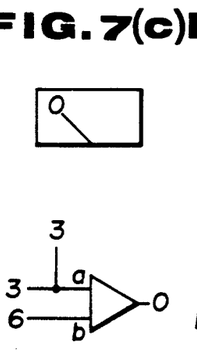
Figure 7D:
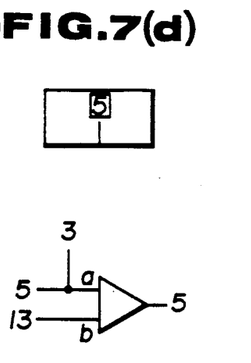

FIG. 4 shows the comparator (16 in FIG. 1) and the memory circuit 24 is reset to zero (no change occurs in this case) and then stores the difference 1. This state is shown in FIG. 6(b). Since 1, as a bias, is added to the terminal "a", the output of the adder-subtractor 21 becomes 0. The measuring needle 3 is advanced from the region I into the region II until the difference in the output reaches the above-mentioned constant value, i.e. 5 in the case shown. Now, it may be recognized that the needle's tip is at the apex of the tooth's root (see FIG. 6(c)). The next measurement will be explained with reference to FIG. 7. At a next starting moment (FIG. 7(a)), the initial setting is not always the same as shown in FIG. 6(a), if the state of a root canal of a tooth differs or the patient is changed. As shown in FIG. 7(a), assume that the terminals "a" and "b" are initially set to 3 and 6 respectively, and the memory circuit 24 stores 1. Therefore the output of the amplifier 22 is equal to 2. When the reset push-button 29 is pressed, the erasing circuit 25 is started by an erasing pulse to firstly reset the memory circuit 24 to zero. As a result the output of the adder-subtractor 21 becomes 3 as shown in FIG. 7(b). A storing pulse is then produced to make the memory circuit 24 store the difference in value of 3. Consequently, a bias of 3 is applied to the terminal "a" as shown in FIG. 7(c), and the position of an apical foramen can be detected when the indicator indicates a value of 5 as shown in FIG. 7(d). In FIGS. 6 and 7, a figure of 5 is adopted as a constant only for the sake of explaining clearly and is meaningless in itself. In practice, the specified value is marked on the following circuits. In FIG. 4, numeral 21 is an adder-subtractor (comparator 16), 22 is an amplifier, 23 is an indicator, 24 is a memory circuit, 25 is an erasing circuit, 26, 27 and 28 are pulse generators. When an output signal for a frequency of 1KHz and an output signal for a frequency of 5KHz are applied to terminals "a" and "b" respectively, the differential output voltage is produced by the adder-subtractor 21 and amplified by the amplifier 22 through which it is transmitted and indicated on the indicator 23. The memory circuit 24 stores the output of the amplifier 22 by the action of a storing pulse from the pulse generator 26 and it is reset by a signal from the erasing circuit 25. The pulse generator 27 produces an erasing pulse for driving the erasing circuit 25. The pulse generators 26 and 27 are actuated by a reset pulse from the pulse generator 28 when a reset switch 29 is pressed. A storing pulse is produced next to the erasing pulse as shown in FIG. 5. The value stored in the memory circuit is applied as a bias value to one of two inputs, for example, the input terminal "a".

FIGS. 6 and 7 are views for explaining the operations of the device shown in FIG. 4. In FIGS. 6 and 7, numerals (I) and (II) indicate an indicator and an adder-subtractor respectively. In FIG. 6, at the moment of starting (a) the value stored in the memory circuit 24 is 0, and the output of the adder-subtractor 21 becomes 1 when the voltage values 2 and 3 are applied to the terminals "a" and "b" respectively. When the reset pushbutton 29 is pressed, the meter's scale and the position of the root's apex is monitored when the meter's pointer coincides with the marked point of the scale.

As mentioned above, according to the above-described embodiment, since the position of an apical foramen is determined at the moment when a difference between two outputs having respective frequency responses becomes a specified constant value, the detection can be easily and properly performed in comparison with the prior art. However, the above-mentioned embodiment requires pressing the reset button every time an apical foramen's position has been detected which reduces its working efficiency.

Figure 8:
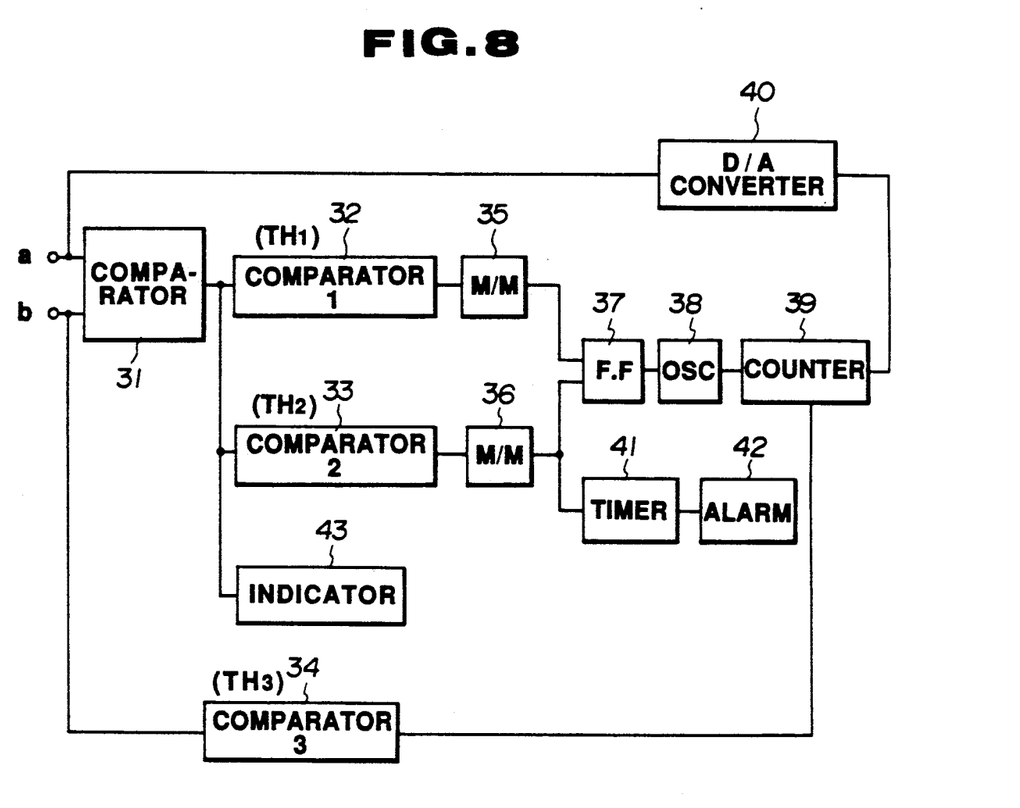
FIG. 8 is a view for explaining another embodiment of the present invention.

FIG. 8 relates to another embodiment of a device for detecting the position of an apical foramen of a tooth's root wherein the above-mentioned drawbacks are eliminated and the outputs (a) and (b) can be equalized to each other without pressing the reset button, i.e. zero adjustment can be automatically realized.

FIG. 8 is a construction view for explaining another embodiment of the present invention, which comprises a "difference" detection circuit 31, comparators 32, 33, 34, one-shot trigger (mono/multi) circuits 35, 36, a flip-flop circuit 37, a pulse oscillator 38, a counter 39, a D/A converter 40, a timer 41, an alarm 42 and an indicator 43.

Figure 9:
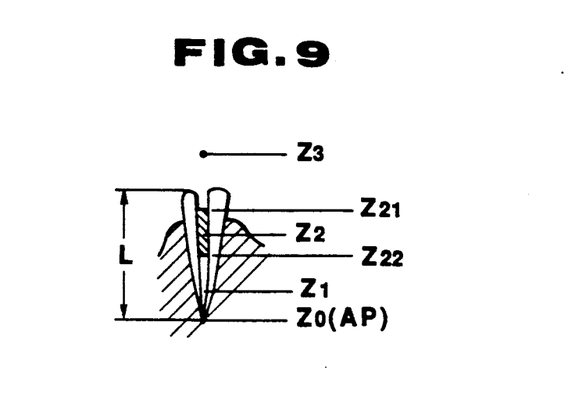
FIG. 9 is a view showing the relative positions of a measuring needle inside of a tooth's root canal.

FIG. 9 is a view showing the relative positions of a measuring needle inside a tooth's root canal. In FIG. 9, Z3 indicates the position of the measuring needle before being inserted into the root canal, Z2 indicates the "zero" adjusting area of the tooth's root canal wherein the measuring needle is inserted and zero adjustment is achieved as later described, Z1 indicates the measuring area of the root canal wherein after the zero adjustment, the measuring needle is further inserted toward the root canal's apex starting from zero point and Z0 indicates the position of the apical foramen.

Figure 10:
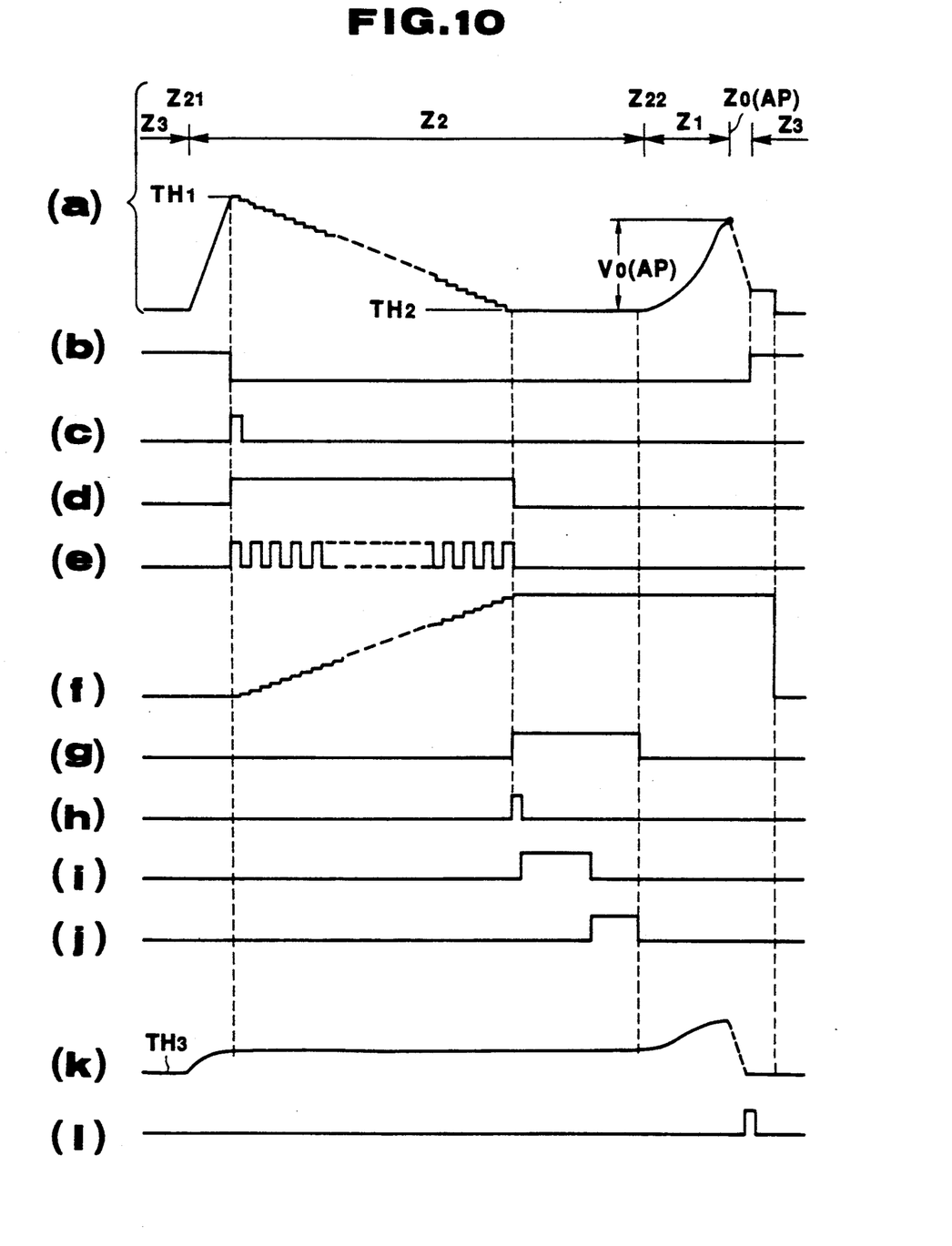
FIG. 10 is a time chart for explaining the operations of the embodiment shown in FIG. 8.

FIG. 10 is a time chart for explaining the operations of the embodiment shown in FIG. 8, and FIG. 10(a) shows the relationship between the above-mentioned positions of the measuring needle which correspond to the output signals of the difference in the detection circuit 31.

First, the condition before the insertion of the measuring needle 3 into a tooth's root canal 2 is considered. In this state, both input voltages of the "difference" detection circuit 31 are equal to each other and therefore the "difference" detection circuit 31 has zero voltage at its output.

When the measuring needle 3 from the above-mentioned state is inserted into the tooth's root canal 2, voltages which correspond to an impedance in the root canal, according to their frequency responses, appear at the respective input terminals "a" and "b" of the "difference" detection circuit 31. The output voltage of the "difference" detection circuit 31 varies before and after the insertion of the measuring needle 3 into the tooth's root canal 2. A change in the "difference" output voltage is picked up by the first comparator 32 (FIG. 10(b)), and when the "difference" output voltage exceeds the threshold level (TH1) of the comparator 32, the "one-shot" trigger (mono/multi) circuit 35 activates (FIG. 10(c)) and actuates by its output signal the flip-flop circuit 37 which in turn operates by its output signal the pulse oscillator 38 (FIG. 10(e)). An output pulse of the pulse oscillator 38 is counted by the counter 39 (FIG. 10(f)) and the counter output is converted into an analog value by the D/A converter 40 and it is then fed back to one of the input terminals of the "difference" detection circuit 31 to adjust its output to zero by adding (or subtracting) the value to (or from) the input. When the output voltage of the "difference" detection circuit 31 is adjusted to zero, the second comparator 33 operates (FIG. 10(g)) to activate the "one-shot" trigger (mono/multi) circuit 36 (FIG. 10(h)), invert the flip-flop circuit 37 (FIG. 10(d)), stop the pulse oscillator 38 (FIG. 10 (e)) and stop the counter 39 which holds the counted value (FIG. 10(f)). As soon as the zero output of the "difference" detection circuit 31 is detected by the comparator 33 or the time preset by the timer 41 is elapsed (FIG. 10(i)), the alarm 42 activates to inform that the zero adjustment has been accomplished (FIG. 10 (j)). As the measuring needle 3 is further inserted into the tooth's root canal 2 after the alarm is being confirmed, the reading of the indicator 43 gradually increases in accordance with an increase of the difference between voltages at the input terminals "a" and "b" of the "difference" detection circuit 31. When the indicator 43 indicates the marked scale value VO (AP) corresponding to the position of the apical foramen (FIG. 10(a)), it may be concluded that the tip of the measuring needle 3 has reached the position (Z0) of the root's apex since the value VO (AP) is common to all persons with no individual variations. Accordingly, it is possible to know the root canal's length by measuring the inserted length L of the measuring needle 3. When the measuring needle 3 is pulled out of the tooth's root canal 2, the output voltage of the "difference" detection circuit 31 becomes equal to the output voltage of the D/A converter 40, and a change in the input signal at the input terminal "b" (FIG. 10(k)) is detected by the third comparator 34 (FIG. 10(l)) which in turn resets its output, the counter 39 (FIG. 10(f)), into its initial state (FIG. 10(a)).

As is apparent from the fore-going description, according to the present invention it may be possible to provide an easily operable gauge for measuring a root canal's length and which can automatically conduct the zero adjustment for a short time after the insertion of the measuring needle into the tooth's root canal and then inform of the completion of the zero adjustment by means of an alarm.

I claim:

1. In a device for detecting the position of an apical foramen of a tooth's root for use in dental treatment, said device including a source of first and second signals of different frequency, first and second detection circuits connected to detect a change in the amplitudes of the respective frequencies, a "difference" detection circuit connected to compare the outputs of the detection circuits to successively produce a "difference" signal, and indicating means coupled to the output of said "difference" detection circuit; the improvement comprising a bias voltage memory circuit, a signal generator including means for generating a reset signal, means connected to store a signal in said bias voltage memory circuit according to the output of the "difference" detection circuit, in response to said reset signal, and means connected to superimpose a voltage corresponding to said signal stored in said memory on the output of only one said detection circuits.

2. The device of claim 1, wherein said signal generator further comprises a source of pulses connected to said memory to erase the signal stored in the bias voltage memory circuit and to subsequently output said reset signal.

3. The device of claim 2, wherein the "difference" detection circuit comprises means for setting its output to zero in response to the superimposition of the voltage stored in the memory circuit to the "difference" detection circuit's input.

4. The device of claim 3, wherein said indicating means comprises a meter having a scale with a mark of a predetermined value.

5. In a device for detecting the position of an apical foramen of a tooth's root, for use in dental treatment, which includes a source of first and second signals of different frequency, first and second detection circuits connected to detect a change in the amplitude of the respective frequencies, a "difference" detection circuit connected to compare the outputs of the detection circuits to successively produce a "difference" signal, and indicating means coupled to the output of said "difference" detection circuit; the improvement comprising a feedback circuit connected to feed the output of the "difference" detection circuit to only one of the input terminals of the "difference" detection circuit so as to equalize the two inputs thereof by the addition or subtraction of the output value and thereby to make its output equal to zero, an alarm means connected to announce that the output of the "difference" detection circuit is set to zero, said indicating means connected to indicate that the output of the "difference" detection circuit has reached a predetermined non-zero value.

6. The device of claim 5, wherein the "difference" detection circuit has means for setting its output to zero in response to the application thereto of an output voltage of the feedback circuit and which can increase to a predetermined non-zero value in response to changes in the outputs of said detection circuits.

7. The device of claim 5, wherein the feedback circuit has a pulse generator and a counter connected to add output pulses generated by said pulse generator, means for applying a signal corresponding to the count in said counter to one of the two input terminals of the "difference" detection circuit and means for stopping the pulse generator when the output of the "difference" detection circuit becomes zero.

8. The device of claim 6, wherein the feedback circuit has a pulse generator and a counter connected to add output pulses generated by said pulse generator, means for applying a signal corresponding to the count in said counter to one of the two input terminals of the "difference" detection circuit and means for stopping the pulse generator when the output of the "difference" detection circuit becomes zero.

* * * * *